US005989213A

United States Patent [19]
Maginot

[11] Patent Number: 5,989,213
[45] Date of Patent: Nov. 23, 1999

[54] LONG-TERM DIALYSIS CATHETER SYSTEM AND ASSOCIATED METHOD

[75] Inventor: Thomas J. Maginot, Crown Point, Ind.

[73] Assignee: Maginot Vascular Systems, Crown Point, Ind.

[21] Appl. No.: 09/078,834

[22] Filed: May 14, 1998

Related U.S. Application Data

[60] Provisional application No. 60/070,583, Jan. 6, 1998.

[51] Int. Cl.$^6$ .................................................. A61M 1/00
[52] U.S. Cl. .............................. 604/28; 604/29; 604/500; 604/43; 604/175
[58] Field of Search ..................................... 604/500, 506, 604/507, 508, 43, 44, 19, 21, 93, 174, 175, 28, 29

[56] References Cited

U.S. PATENT DOCUMENTS

| | | | |
|---|---|---|---|
| 4,468,216 | 8/1984 | Muto | 604/43 |
| 4,493,696 | 1/1985 | Uldall | 604/43 |
| 4,738,667 | 4/1988 | Galloway . | |
| 5,053,023 | 10/1991 | Martin | 604/280 |
| 5,156,592 | 10/1992 | Martin et al. | 604/43 |
| 5,236,424 | 8/1993 | Imran . | |
| 5,405,323 | 4/1995 | Rogers et al. | 604/53 |
| 5,417,669 | 5/1995 | Castaneda | 604/264 |
| 5,498,240 | 3/1996 | Bagaoisan et al. | 604/96 |
| 5,514,112 | 5/1996 | Chu et al. | 604/267 |
| 5,569,182 | 10/1996 | Twardowski et al. | 604/43 |
| 5,569,204 | 10/1996 | Cramer | 604/164 |

OTHER PUBLICATIONS

Marketing brochure entitled "Uldall Double Lumen Hemodialysis Catheter Trays", Cook Critical Care, A Division of Cook Incorporated, P.O. Box 489, Bloomington, Indiana 47402, 1994.

Interventional Radiology, vol. One, Second Edition, Published by Williams & Wilkins, 428 East Preston Street, Baltimore, Maryland 21202, pp. 366–367: 1992.

*Primary Examiner*—John D. Yasko
*Attorney, Agent, or Firm*—Maginot, Addison & Moore

[57] ABSTRACT

A long-term dialysis catheter system for use in a body of a patient includes a guide catheter having a guide lumen defined therein, wherein the guide lumen defines a distal guide orifice. The system also includes a tissue ingrowth member secured to an outer surface of the guide catheter. The system further includes an original dialysis catheter positionable between an original inserted position and an original removed position, wherein (i) the original dialysis catheter has an original ingress lumen and an original egress lumen defined therein, (ii) the original ingress lumen defines an original distal ingress orifice, and (iii) the original egress lumen defines an original distal egress orifice. The system also includes a replacement dialysis catheter positionable between a replacement inserted position and a replacement removed position, wherein (i) the replacement dialysis catheter has a replacement ingress lumen and a replacement egress lumen defined therein, (ii) the replacement ingress lumen defines a replacement distal ingress orifice, and (iii) the replacement egress lumen defines a replacement distal egress orifice. The original distal ingress orifice and the original distal egress orifice are positioned on an original distal segment of the original dialysis catheter which extends out of the distal guide orifice of the guide catheter when the original dialysis catheter is positioned within the guide lumen of the guide catheter. The replacement ingress orifice and the replacement egress orifice are positioned on a replacement distal segment of the replacement dialysis catheter which extends out of the distal guide orifice of the guide catheter when the replacement dialysis catheter is positioned within the guide lumen of the guide catheter. A medical procedure utilizing the long-term dialysis catheter system is also disclosed.

9 Claims, 8 Drawing Sheets

LONG-TERM DIALYSIS CATHETER SYSTEM AND ASSOCIATED METHOD

This application claims the benefit of U.S. Provisional Application Ser. No. 60/070,583, filed Jan. 6, 1998.

BACKGROUND OF THE INVENTION

The present invention relates generally to dialysis catheters, and more particularly to a long-term dialysis catheter system for use in a body of a patient and an associated method of maintaining blood flow in the catheter system.

Various medical procedures require that a patient be catheterized. For example, catheterization may be required when a patient undergoes hemodialysis or has a clot aspirated from a blood vessel. Generally, the length of time the patient will be catheterized dictates whether a physician will utilize a "temporary catheterization technique" (i.e. a technique in which the catheter is left in a blood vessel for a relatively short period of time such as a few minutes, hours, days, or weeks) or a "permanent catheterization technique" (i.e. a technique in which the catheter is left in a blood vessel for a relatively long period of time such as several months or indefinitely).

For example, a procedure in which a clot is aspirated from a blood vessel typically includes placing the catheter in the blood vessel for a relatively short period of time such as a few minutes to a few hours and then withdrawing the catheter once the clot has been removed. Therefore, when performing such an aspiration procedure, it is common for a physician to use the temporary catheterization technique to place the catheter in the blood vessel of the patient.

On the other hand, when a procedure is performed to effect hemodialysis, a physician may place a catheter in the blood vessel for a relatively long period of time. In particular, a patient suffering from kidney failure who is involved in a hemodialysis regimen typically requires a dialysis session three days per week for an indefinite period of time whereby extra fluid, chemicals, and wastes are removed from his/her body. A patient who is involved in such a hemodialysis regimen may need a catheter placed in his/her blood vessel for a relatively long period of time in order to provide a ready means for vascular access into his/her bloodstream over such relatively long period of time. This long term placement of the catheter for dialysis purposes may be desirable for a number of reasons.

Firstly, a patient may have experienced progressive loss of other conventional long term vascular access possibilities such as surgically created arteriovenous fistulas. Accordingly, the long term placement of the catheter in the patient's blood vessel may be the best alternative for the patient as he/she proceeds with the hemodialysis regimen.

Additionally, the long term placement of the catheter in the patient's blood vessel may be desirable after initial creation of an arteriovenous fistula in the patient's body. In particular, it is desirable to provide a ready means for vascular access into the patient's bloodstream during a maturation period of the arteriovenous fistula. The maturation period allows the arteriovenous fistula to develop sufficiently so that it will function as a ready means for vascular access into the patient's bloodstream which may be safely punctured multiple times per week for hemodialysis. The length of time of this maturation period is typically on the order of several weeks (e.g. three weeks) to many months (e.g. six months).

Therefore, when performing a hemodialysis procedure, it is common for a physician to use the permanent catheterization technique to place the catheter in the blood vessel of the patient.

These two catheterization techniques are significantly different with respect to their complexity and degree of invasiveness. For example, in the case of the temporary catheterization technique, it is common to insert a temporary catheter into a patient's blood vessel using a "direct puncture technique." This technique entails creating a small incision in a patient's skin with a scalpel directly over the blood vessel to be catheterized. A needle is then advanced through the skin incision and subcutaneous tissue and into the blood vessel. Thereafter, a guidewire is advanced through the needle into the blood vessel and the needle is subsequently removed over the guidewire. Then, one or more tubular vessel dilators are used to widen the opening defined in the skin and subcutaneous tissue, and further to widen the opening defined in the blood vessel wall to a caliber similar to that of the temporary catheter. The temporary catheter is then advanced over the guidewire and into the blood vessel. Thereafter, the guidewire is removed.

When the temporary catheterization technique is used during a clot aspiration procedure, two catheters are usually placed in the blood vessel of a patient. In particular, an outer catheter is usually placed within the blood vessel using the above described direct puncture technique so that its distal opening is located near the clot. Thereafter, an inner catheter having a smaller caliber relative to the outer catheter is advanced through a lumen of the outer catheter. While the inner catheter is positioned within the outer catheter, an aspiration vacuum is applied to the inner catheter with a syringe. If the size of the clot (or fragments thereof) are smaller than the inner diameter of the inner catheter, then the clot or clot fragments are drawn into and through the inner catheter thereby removing the clot from the blood vessel. If the size of the clot or clot fragments are larger than the inner diameter of the inner catheter, then the clot or clot fragments are drawn to a location adjacent to the distal orifice of the inner catheter. Subsequently, while the aspiration vacuum is still being applied, the inner catheter is withdrawn from the outer catheter thereby additionally withdrawing the clot or clot fragments from the outer catheter and the patient's blood vessel. Thereafter, the outer catheter remains temporarily in place within the blood vessel of the patient for subsequent injections of radiographic contrast for imaging purposes to determine the extent of clot remaining in the blood vessel as well as to determine if clot has migrated to another location within the blood vessel. The outer catheter, which remains temporarily in place in the blood vessel, provides a conduit for the inner catheter to be advanced back into the patient's blood vessel for additional aspiration attempts which are usually required for complete removal of the clot from the blood vessel.

If an outer catheter needs to be replaced during a clot aspiration procedure because of catheter malfunction, such replacement can be accomplished by advancing a guidewire through the lumen of the outer catheter and into the blood vessel. The existing outer catheter can then be removed over the guidewire to a location outside of the patient's body. Thereafter, a new outer catheter is placed in the patient's blood vessel by advancing the new outer catheter over the guidewire as discussed above.

In contrast to the temporary catheterization technique, the permanent catheterization technique typically entails inserting a permanent catheter into a patient's blood vessel using a "tunneled catheter technique." The tunneled catheter technique includes (i) creating a first opening by making a small incision in a patient's skin with a scalpel directly over the blood vessel to be catheterized, (ii) puncturing the blood vessel at a location directly below the first opening by advancing a needle through the skin incision and subcutaneous tissue and into the blood vessel, (iii) advancing a guidewire through the needle into the blood vessel, (iv) removing the needle over the guidewire, (v) passing one or more tubular vessel dilators over the guidewire to widen the opening defined in the skin and subcutaneous tissue, and further to widen the opening defined in the blood vessel wall to a caliber similar to that of the tubular guide, (vi) advancing the tubular guide over the guidewire and into the blood vessel, (vii) thereafter, creating a second opening in the patient's skin spaced apart at least several centimeters from the first opening, (viii) advancing a tunneling instrument from the second opening to the first opening so as to create a passageway within the subcutaneous tissue under the skin between the first opening and the second opening, (ix) advancing a permanent catheter having a tissue ingrowth member attached to an outer surface thereof into the second opening and through the passageway such that a distal end of the permanent catheter is located adjacent the first opening, (x) inserting the distal end of the permanent catheter through the tubular guide member and into the blood vessel to be catheterized whereby the tissue ingrowth member is positioned in the subcutaneous tissue, (xi) removing the tubular guide member, and (xii) closing the first opening with suture whereby the permanent catheter (a) is no longer exposed through the first opening, (b) extends for at least several centimeters under the patient's skin between second opening and the location where the permanent catheter enters the blood vessel, and (c) extend outs of the second opening so that a proximal end of the permanent catheter is located outside of the patient's body.

In contrast to the direct puncture catheter technique, the tunneled catheter technique results in the placement of a catheter in a patient's body in a manner which allows the catheter to remain safely in the patient's body for a relatively long period of time. For example, a degree of safety is achieved by separating the following two openings by at least several centimeters: (i) the skin opening through which the catheter enters the patient's body, and (ii) the blood vessel opening through which the catheter enters the patient's vascular system. This safety feature decreases the likelihood that bacteria will migrate up the length of the catheter from the skin opening and cause an infection at the blood vessel opening.

In addition, another degree of safety is achieved by providing a tissue ingrowth member which is attached to and extends around an outer surface of the catheter. As the catheter is left in the patient's body over a period of time, the tissue ingrowth member becomes affixed to the subcutaneous tissue of the patient's body thereby providing a secure attachment of the catheter to the patient's body. Providing a secure attachment between the catheter and the patient's body reduces the likelihood that the catheter will be inadvertently removed or withdrawn from the patient's body. Moreover, since the subcutaneous tissue becomes attached to the tissue ingrowth member, a physical barrier is created between following two openings: (i) the skin opening through which the catheter enters the patient's body, and (ii) the blood vessel opening through which the catheter enters the patient's vascular system. This physical barrier further decreases the likelihood that bacteria will migrate up the length of the catheter from the skin opening and cause an infection at the blood vessel opening.

While the tunneled catheter technique provides the significant advantage of allowing the catheter to remain safely in the patient's body for a relatively long period of time, significant disadvantages of the tunneled catheter technique exists. For example, when a catheter remains in a blood vessel for a long period of time, there is a tendency for blood clots including fibrin (e.g. in the form of a fibrin sheath) to attach to and build-up on the outer and inner surfaces of the portion of the catheter which is located within the blood vessel. The above described attachment and build-up tends to occlude the various distal openings defined in the catheter which enable fluid movement into and out of the catheter. For instance, attempts at withdrawing blood through the catheter may be unsuccessful due to blood clots creating a "ball-valve" effect which occlude the various distal openings of the catheter.

When occlusion of the various distal openings of the catheter occurs due to the above described blood clot attachment and build-up, a physician has several options for eliminating the occlusion thereby reestablishing access to the vascular system. One option is to remove the occluded catheter and replace it with a new catheter. However, in contrast to the ease of exchanging a catheter which was placed in the patient's body using the direct puncture technique, exchanging a catheter which was placed in the patient's body using the tunneled catheter technique is substantially more complicated and invasive. This is true since in order to remove the occluded catheter from the patient's body, the physician must surgically dissect the tissue ingrowth member which is secured to the outer surface of the catheter from the patient's subcutaneous tissue. Recall that the tissue ingrowth member becomes affixed to the subcutaneous tissue over a period of time. Thereafter, the physician would place a new catheter into the patient's body generally using the above described tunneled catheter technique. Therefore, this option is undesirable since it requires additional surgery which further traumatizes the patient and increases the cost of the medical care.

Another option for eliminating the occlusion of the various distal openings of the catheter in order to reestablish access to the vascular system involves the performance of a medical procedure in which a blood clot-dissolving medication such as urokinase is infused into the catheter. However, this medication is not always successful in eliminating the occlusion of the various distal openings of the catheter. In addition, infusion of the medication into the catheter subjects the patient to potential bleeding complications due to the medication entering the vascular system and being circulated systemically. Further, this medication is expensive. Thus, this option has serious drawbacks as well.

An additional option openings the occlusion of the various distal openings of the catheter in order to reestablish access to the vascular system involves the performance of a medical procedure in which an intravascular snare is introduced into the blood vessel in order to physically strip off any blood clots or fibrin sheath which has attached and built-up on the distal portion of the catheter. However, for catheters placed in veins, this medical procedure requires a venopuncture in the femoral or jugular vein which is invasive and can be uncomfortable for a patient. Furthermore, this option requires the use of (i) an intravascular snare, (ii) a physician experienced in catheter techniques, and (iii) an angiographic suite to provide fluoroscopic imaging. Use of each of items (i), (ii), and (iii) above causes this option to be relatively expensive. Consequently, this option also has significant disadvantages.

What is needed therefore is a method and apparatus for eliminating the occlusion of the various distal openings of a catheter which has been placed in a patient's body using the tunneled catheter technique which overcomes one or more of the above-mentioned drawbacks.

SUMMARY OF THE INVENTION

In accordance with one embodiment of the present invention, there is provided a method of maintaining blood flow in a long-term dialysis catheter system which includes (i) a guide catheter having a tissue ingrowth member secured thereto, (ii) an original dialysis catheter having an original distal ingress orifice and an original distal egress orifice, and (iii) a replacement dialysis catheter having a replacement distal ingress orifice and a replacement distal egress orifice. The method includes the steps of advancing a guide catheter into a body of a patient so that (i) a distal guide orifice of the guide catheter is positioned within a blood vessel of the body, and (ii) the tissue ingrowth member is positioned in subcutaneous tissue of the body. The method further includes the step of advancing the original dialysis catheter though a guide lumen of the guide catheter so that the original distal ingress orifice and the original distal egress orifice are advanced out of the distal guide orifice and positioned within the blood vessel. In addition, the method includes the step of performing an original dialysis procedure on the patient with the original dialysis catheter after the original dialysis catheter advancing step. The method also includes the step of leaving the guide catheter within the body for a period of time sufficient to cause the subcutaneous tissue to become affixed to the tissue ingrowth member which is secured to the guide catheter. Further, the method includes the step of removing the original dialysis catheter from the guide lumen of the guide catheter. The method additionally includes the step of advancing the replacement dialysis catheter though the guide lumen of the guide catheter so that the replacement distal ingress orifice and the replacement distal egress orifice are advanced out of the distal guide orifice and positioned within the blood vessel. The method further includes the step of performing a subsequent dialysis procedure on the patient with the replacement dialysis catheter after the replacement dialysis catheter advancing step.

Pursuant to another embodiment of the present invention, there is provided a long-term dialysis catheter system for use in a body of a patient which includes a guide catheter having a guide lumen defined therein, wherein the guide lumen defines a distal guide orifice. The system also includes a tissue ingrowth member secured to an outer surface of the guide catheter and configured to facilitate fibrous tissue growth therein, whereby subcutaneous tissue of the body becomes affixed to the tissue ingrowth member when the tissue ingrowth member remains in contact with the subcutaneous tissue over a period of time. The system further includes an original dialysis catheter positionable between an original inserted position and an original removed position, wherein (i) the original dialysis catheter has an original ingress lumen and an original egress lumen defined therein, (ii) the original ingress lumen defines an original distal ingress orifice, and (iii) the original egress lumen defines an original distal egress orifice. The system also includes a replacement dialysis catheter positionable between a replacement inserted position and a replacement removed position, wherein (i) the replacement dialysis catheter has a replacement ingress lumen and a replacement egress lumen defined therein, (ii) the replacement ingress lumen defines a replacement distal ingress orifice, and (iii) the replacement egress lumen defines a replacement distal egress orifice. The original distal ingress orifice and the original distal egress orifice are positioned on an original distal segment of the original dialysis catheter which extends out of the distal guide orifice of the guide catheter when the original dialysis catheter is positioned within the guide lumen of the guide catheter. The replacement ingress orifice and the replacement egress orifice are positioned on a replacement distal segment of the replacement dialysis catheter which extends out of the distal guide orifice of the guide catheter when the replacement dialysis catheter is positioned within the guide lumen of the guide catheter.

It is therefore an object of the present invention to provide a new and useful long-term dialysis catheter system for use in a body of a patient.

It is another object of the present invention to provide an improved long-term dialysis catheter system for use in a body of a patient.

It is a further object of the present invention to provide a new and useful method of maintaining blood flow in a long-term dialysis catheter system.

It is still another object of the present invention to provide an improved method of maintaining blood flow in a long-term dialysis catheter system.

It is yet another object of the present invention to provide a long-term dialysis catheter system and an associated method that does not require additional surgery in order to remove and replace an associated dialysis catheter.

It is moreover another object of the present invention to provide a long-term dialysis catheter system and an associated method which does not require dissection of the tissue ingrowth member of a dialysis catheter in order to remove and replace an associated dialysis catheter.

It is additionally another object of the present invention to provide a long-term dialysis catheter system and an associated method which is relatively less invasive in order to remove and replace an associated dialysis catheter.

It is further another object of the present invention to provide a long-term dialysis catheter system and an associated method which is relatively less expensive in order to remove and replace an associated dialysis catheter.

It is moreover another object of the present invention to provide a long-term dialysis catheter system and an associated method which is relatively safer in order to remove and replace an associated dialysis catheter.

It is yet another object of the present invention to provide a long-term dialysis catheter system and an associated method which is relatively less complicated in order to remove and replace an associated dialysis catheter.

It is further another object of the present invention to provide a long-term dialysis catheter system and an associated method which is relatively less traumatic in order to remove and replace an associated dialysis catheter.

It is still another object of the present invention to provide a long-term dialysis catheter system and an associated method which does not require the infusion of a clot-dissolving medication such as urokinase into the patent's body in order to remove and replace an associated dialysis catheter.

It is yet another object of the present invention to provide a long-term dialysis catheter system and an associated method which does not require the use of an intravascular snare in order to remove and replace an associated dialysis catheter.

It is moreover another object of the present invention to provide a long-term dialysis catheter system and an associated method which does not require use of an angiographic suite in order to remove and replace an associated dialysis catheter.

It is still another object of the present invention to provide a long-term dialysis catheter system and an associated method which does not require use of fluoroscopic imaging in order to remove and replace an associated dialysis catheter.

It is additionally another object of the present invention to provide a long-term dialysis catheter system and an associated method which does not require blood clot to be stripped off of the catheter in order to remove and replace an associated dialysis catheter.

It is further another object of the present invention to provide a long-term dialysis catheter system and an associated method that does not involve a medical procedure which requires the patient to be subjected to a venopuncture in the femoral or jugular vein in order to remove and replace an associated dialysis catheter.

Other objects and benefits of the present invention can be discerned from the following description and accompanying drawings.

DESCRIPTION OF THE PREFERRED EMBODIMENT

Figure 1:
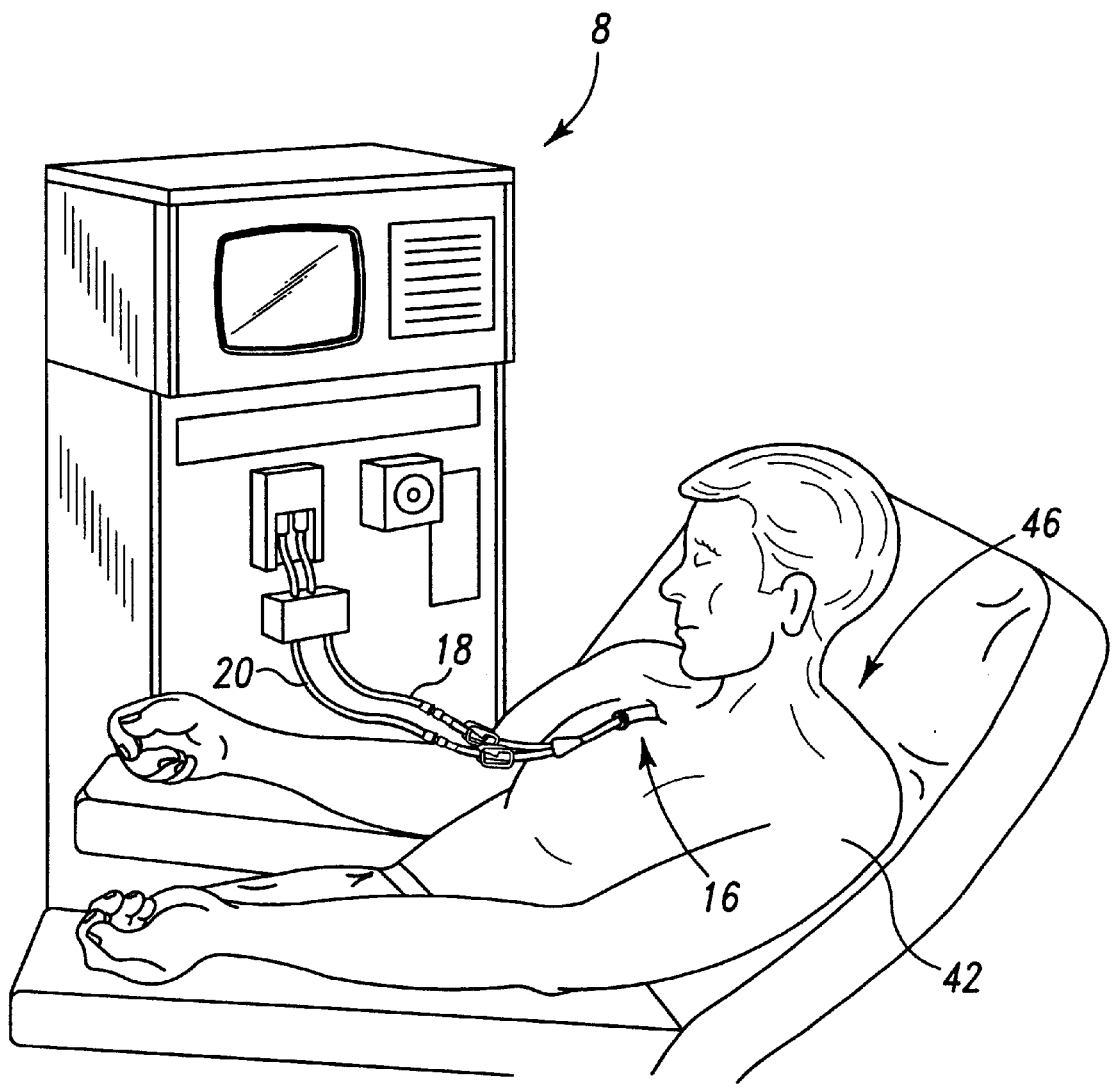
FIG. 1 is a perspective view of a patient undergoing a dialysis procedure utilizing the long-term dialysis catheter system of the present invention.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Referring now to FIG. 1, there is shown a hemodialysis machine 8 to which is attached a long-term dialysis catheter system 16 which incorporates the features of the present invention therein. The catheter system 16 is inserted in a patient's body 46. The hemodialysis machine 8 includes an inlet line 18 and an outlet line 20 which are each in fluid communication with the catheter system 16. The body 46 includes skin, generally indicated by the reference numeral 42. The body 46 further includes subcutaneous tissue 44 positioned below the skin 42 (see FIG. 7).

Figure 2:
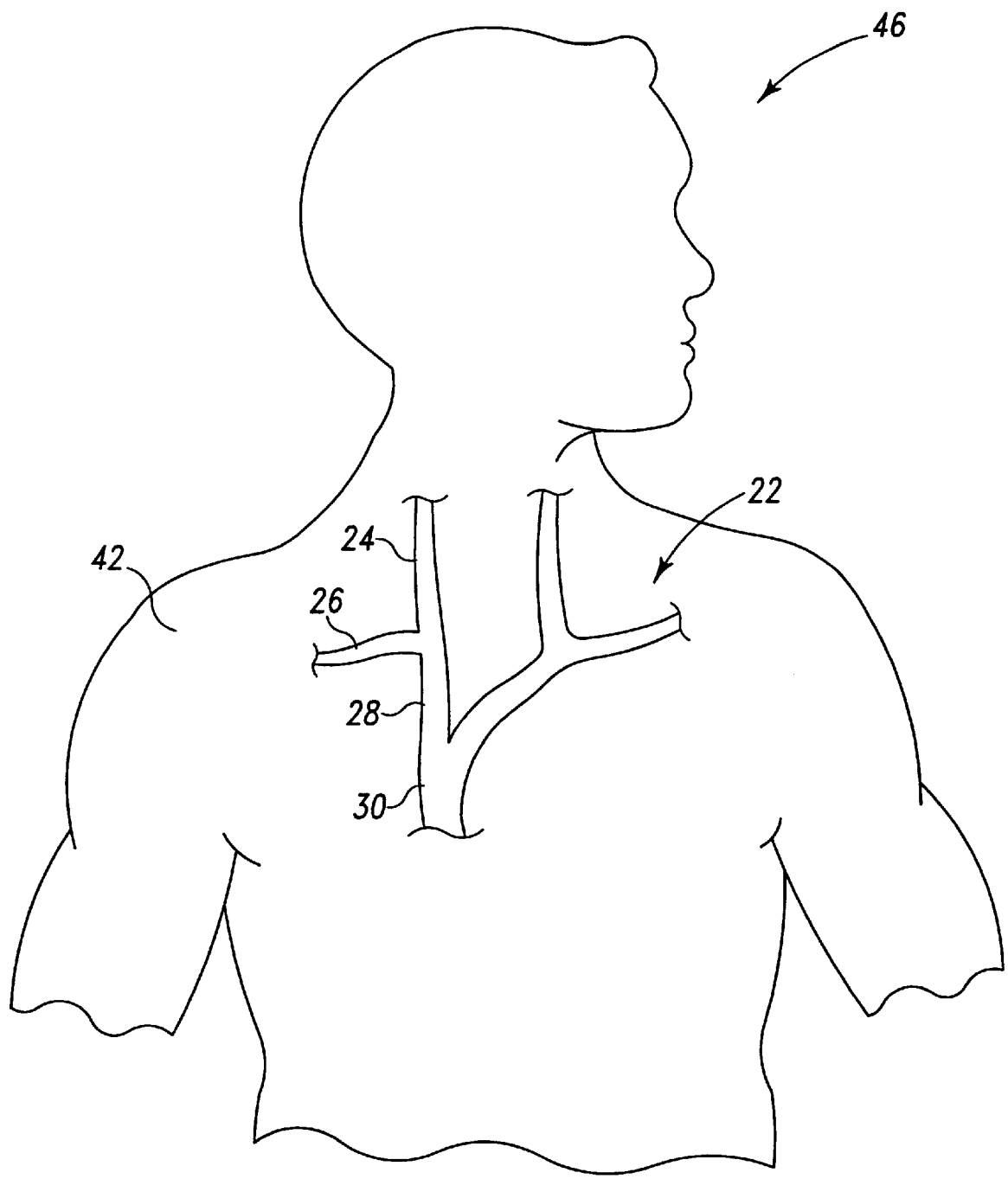
FIG. 2 is a schematic view of a portion of the vascular system of the patient of FIG. 1, showing the right internal jugular vein, the right subclavian vein, the right inominate vein, and the superior vena cava.

As shown in FIG. 2, the body 46 further includes a vascular system 22. The vascular system 22 includes a right internal jugular vein 24, a right subclavian vein 26, a right inominate vein 28, and a superior vena cava 30. Note that the vascular system 22 is positioned within the body 46 underneath the skin 42. However, the vascular system 22, including the right internal jugular vein 24, the right subclavian vein 26, the right inominate vein 28, and the superior vena cava 30, are depicted in FIGS. 2 and 7–10 with solid lines for clarity of description.

Figure 3:
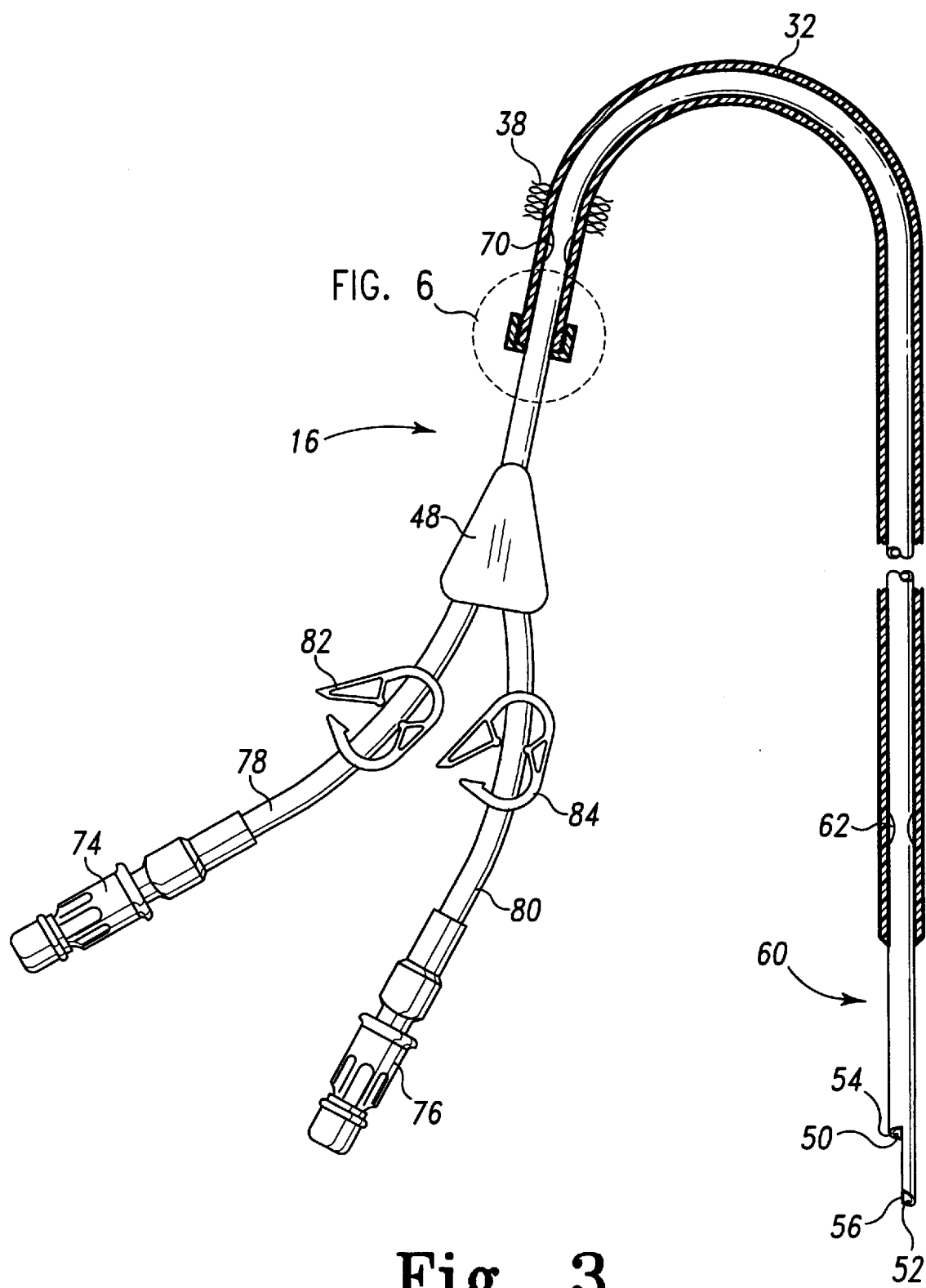
FIG. 3 is an enlarged side elevational view of the long-term dialysis catheter system of FIG. 1, showing the original dialysis catheter positioned within the guide lumen of the guide catheter.

The catheter system 16 is shown in more detail in FIG. 3. In particular, the catheter system includes a guide catheter 32 having a guide lumen 34 which extends the entire length thereof (see also FIGS. 4A–4D). The guide lumen 34 defines a proximal guide orifice 35 and a distal guide orifice 36.

Figure 4A:
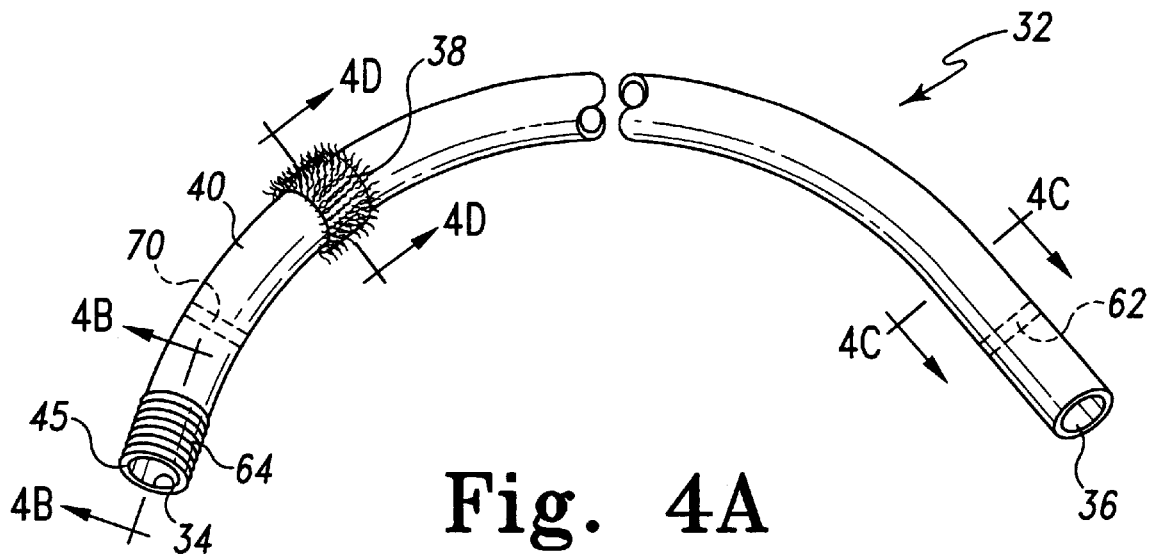
FIG. 4A is an enlarged side elevational view of the guide catheter of the long-term dialysis catheter system shown in FIG. 1.
Figure 4B:
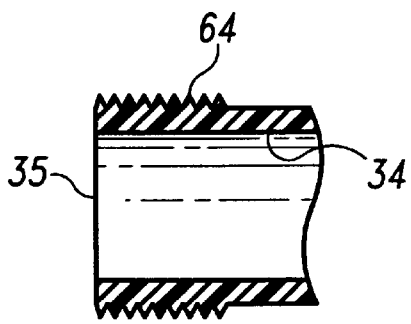
FIG. 4B is an enlarged fragmentary cross sectional view of the guide catheter taken along the line 4B—4B of FIG. 4A as viewed in the direction of the arrows.
Figure 4C:
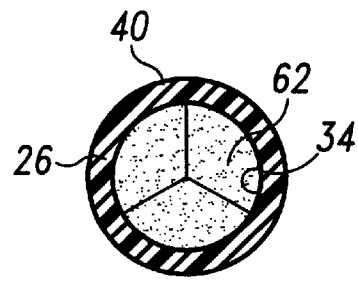
FIG. 4C is an enlarged cross sectional view of the guide catheter taken along the line 4C—4C of FIG. 4A as viewed in the direction of the arrows.
Figure 4D:
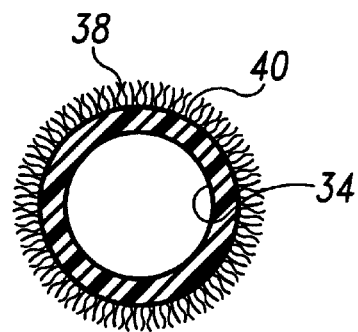
FIG. 4D is an enlarged cross sectional view of the guide catheter taken along the line 4D—4D of FIG. 4A as viewed in the direction of the arrows.

The catheter system 16 further includes a dialysis catheter 48 which is able to be positioned within the guide lumen 34 of the guide catheter 32 (see FIG. 4A). In addition, the catheter system 16 includes a dialysis catheter 58 which is also able to be positioned within the guide lumen 34 of the guide catheter 32 (see FIG. 10). In particular, during a dialysis session, the dialysis catheter 48 is positioned within the guide lumen 34 of the guide catheter 32 for a period of time during which blood is infused and withdrawn therethrough. After the period of time, the blood flow through the lumens of the dialysis catheter 48 may become partially or even totally occluded due to blood clot build-up. In order to remedy this problem, the dialysis catheter 48 is withdrawn from the guide lumen 34 of the guide catheter 32, and thereafter, the dialysis catheter 58 is positioned within the guide lumen 34 of the guide catheter 32 for a subsequent period of time during which blood is infused and withdrawn therethrough. Since the dialysis catheter 48 is originally used in the catheter system 16 and thereafter replaced with the dialysis catheter 58, the dialysis catheter 48 may be characterized as an "original catheter" and the dialysis catheter 58 may be characterized as a "replacement catheter".

Referring again to FIGS. 4A–4D, the guide catheter 32 also includes an outer surface 40 having a tissue ingrowth member 38 secured thereto. Tissue ingrowth member 38 is configured to facilitate fibrous tissue growth therein. More specifically, the subcutaneous tissue 44 of body 46 becomes affixed to the tissue ingrowth member 38 when the tissue ingrowth member 38 remains in contact with the subcutaneous tissue 44 over a period of time. One type of tissue ingrowth member which may be used as the tissue ingrowth member 38 is a DACRON cuff which is available from Bard Access Systems of Salt Lake City, Utah.

The guide catheter 32 further includes a first locking component 64 defined on a proximal end portion thereof. The first locking component 64 includes external threads which cooperate with an internally threaded cap 67 of dialysis catheter 48 to lock the dialysis catheter 48 to the guide catheter 32 as will be discussed in more detail below.

The guide catheter 32 further includes a distal blood flow valve 62 and a proximal blood flow valve 70 positioned within the guide lumen 34. The blood flow valves 62 and 70 are configured to prevent fluid communication between the proximal guide orifice 35 and the distal guide orifice 36 through the guide lumen 34 when neither the dialysis catheter 48 nor the dialysis catheter 58 are positioned within the guide lumen 34. In addition, when either the dialysis catheter 48 or the dialysis catheter 58 is positioned within the guide lumen 34, the blood flow valves 62 and 70 function to prevent blood and/or air leakage through a space defined between the outer surface of the dialysis catheter 48, 58 and the inner surface of the guide catheter 32.

One valve which may be used as either the distal blood flow valve 62 or the proximal blood flow valve 70 with some minor modifications is available from Micro Therapeutics, Inc. of San Clemente, Calif. under the trademark "Cragg MicroValve™".

Referring now to FIGS. 5A–5D, the dialysis catheter 48 includes an ingress lumen 50 and an egress lumen 52 defined therein. The ingress lumen 50 defines a distal ingress orifice 54. Similarly, the egress lumen 52 defines a distal egress orifice 56. The distal ingress orifice 54 and the distal egress orifice 56 are defined in a distal segment 60 of the dialysis catheter 48.

Figure 6:
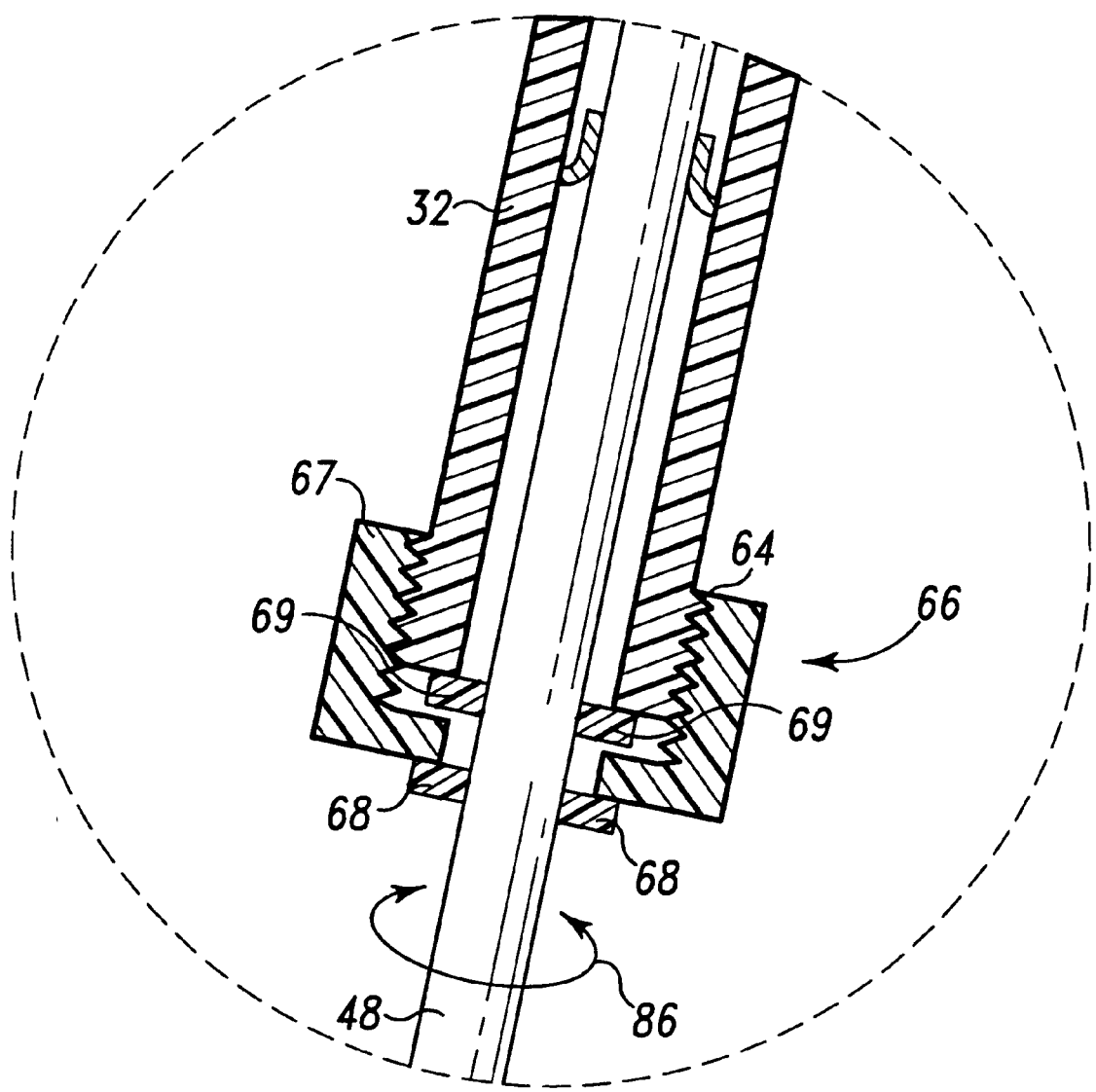
FIG. 6 is an enlarged view of a portion of FIG. 3 which is encircled and indicated as FIG. 6.

The dialysis catheter 48 also includes a second locking component 66 secured thereto. The second locking component 66 cooperates with the first locking component 64 to lock the dialysis catheter 48 to the guide catheter 32. In particular, the second locking component 66 includes the threaded cap 67 which has a hole extending therethrough as shown in FIG. 6. The dialysis catheter 48 may extend through the hole as also shown in FIG. 6. The second locking component 66 further includes an upper tab 68 and a lower tab 69 each which extends around and is secured to the outer surface of the dialysis catheter 48. The cap 67 is interposed between the upper tab 68 and the lower tab 69 so as to be retained therebetween. The threaded cap 67 is able to be rotated relative to the dialysis catheter in the directions indicated by arrow 86 in order to secure/release the dialysis catheter to/from the guide catheter.

The dialysis catheter 48 further includes an egress line 78 and an ingress line 80. The egress line 78 is in fluid communication with the egress lumen 52, while the ingress line 80 is in fluid communication with the ingress lumen 50. The egress line 78 has an adapter 74 attached thereto, and the ingress line 80 has an adapter 76 attached thereto.

Figure 5A:
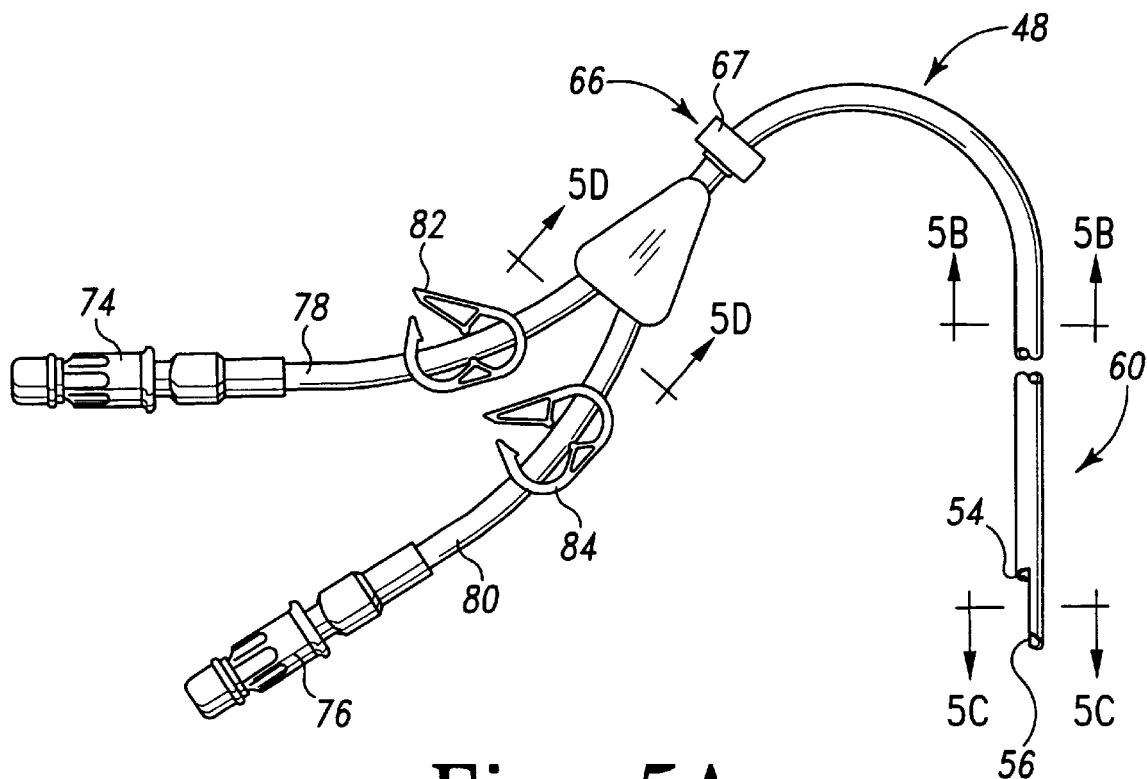
FIG. 5A is an enlarged side elevational view of the original dialysis catheter of the long-term dialysis catheter system shown in FIG. 1.
Figure 5B:
FIG. 5B is an enlarged cross sectional view of the original dialysis catheter taken along the line 5B—5B of FIG. 5A as viewed in the direction of the arrows.
Figure 5C:
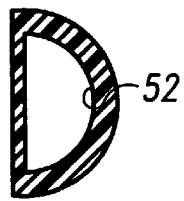
FIG. 5C is an enlarged cross sectional view of the original dialysis catheter taken along the line 5C—5C of FIG. 5A as viewed in the direction of the arrows.
Figure 5D:
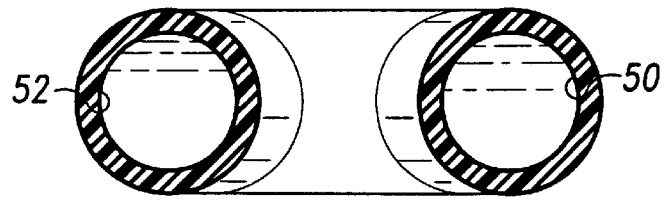
FIG. 5D is an enlarged cross sectional view of the original dialysis catheter taken along the line 5D—5D of FIG. 5A as viewed in the direction of the arrows.

In addition, a clamp 82 is positioned on the egress line 78, while a clamp 84 is positioned on the ingress line 80 as shown in FIG. 5A. It should be understood that closure of the clamp 82 causes fluid communication between adapter 74 and original distal egress orifice 56 to be prevented. Similarly, closure of the clamp 84 prevents fluid communication between the adapter 76 and the distal ingress orifice 54.

The dialysis catheter 48 may be positioned within the guide lumen 34 of the guide catheter 32 as shown in FIG. 3. When the dialysis catheter 48 is positioned within the guide lumen 34 as shown in FIG. 3, the dialysis catheter is said to be positioned in an "inserted position." When the dialysis catheter 48 is entirely removed from the guide lumen 34, the dialysis catheter is said to be positioned in a "removed position."

When the dialysis catheter 48 is positioned in the inserted position, the distal segment 60 of the dialysis catheter 48 extends out of the distal guide orifice 36 of the guide catheter 32. Accordingly, the distal ingress orifice 54 and the distal egress orifice 56 are each positioned outside of guide lumen 34 when the dialysis catheter 48 is located in the inserted position. Moreover, when the dialysis catheter 48 is located in the inserted position, the threaded cap 67 is positioned adjacent to the first locking component 64 such that the threaded cap 67 can be rotated relative to guide catheter 32 so as to lock the second locking component 66 to the first locking component 64. Note that locking the second locking component 66 to the first locking component 64 in the above described manner locks the dialysis catheter 48 to the guide catheter 32.

Figure 8:
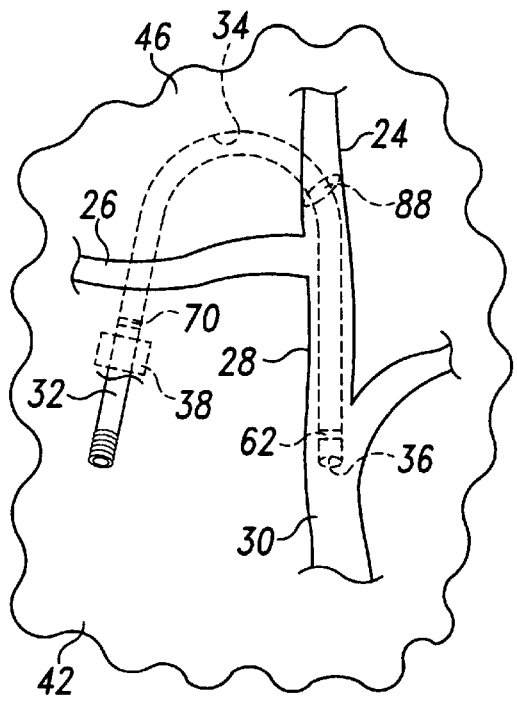
FIG. 8 is a reduced view which is similar to FIG. 7, but showing the original dialysis catheter removed from the guide lumen of the guide catheter.
Figure 9:
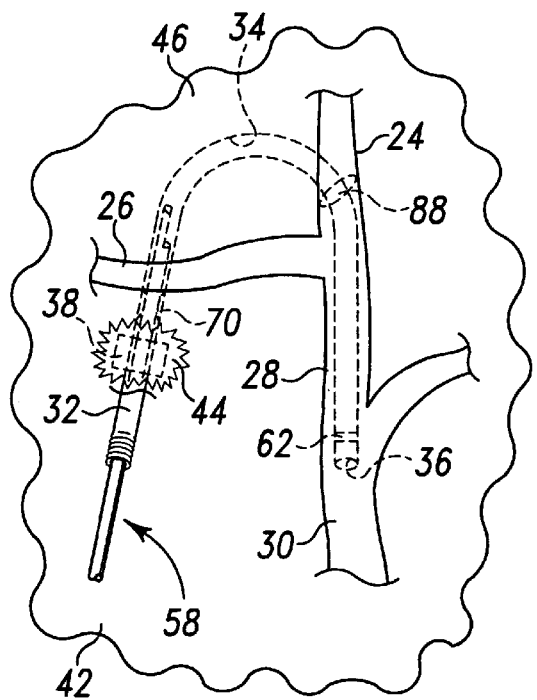
FIG. 9 is a view similar to FIG. 8, but showing a replacement dialysis catheter partially inserted into the guide lumen of the guide catheter.
Figure 10:
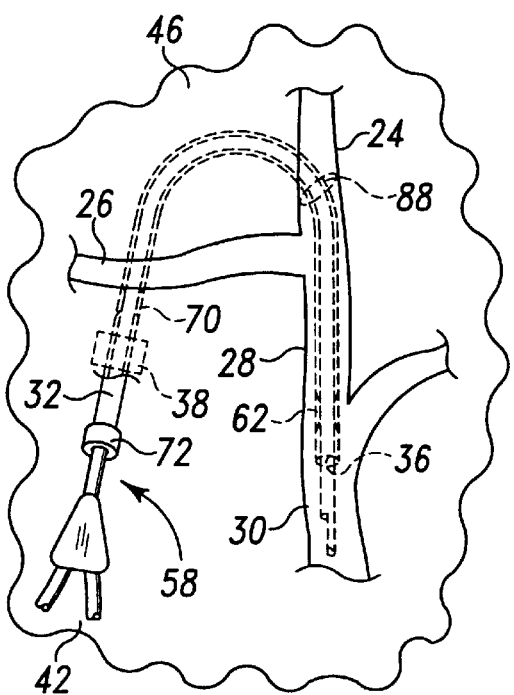
FIG. 10 is a view similar to FIG. 9, but showing the replacement dialysis catheter fully inserted into the guide lumen of the guide catheter.

Referring now to FIGS. 8–10, the structure and use of the dialysis catheter 58 will be described. The dialysis catheter 58 is substantially similar to the dialysis catheter 48. In particular, the dialysis catheter 58 includes an ingress lumen and an egress lumen defined therein. The ingress lumen defines a distal ingress orifice. Similarly, the egress lumen defines a distal egress orifice. The distal ingress orifice and the distal egress orifice are defined in a distal segment of the dialysis catheter 58.

The dialysis catheter 58 also includes a third locking component 72 secured thereto (see FIG. 10). The third locking component 72 cooperates with the first locking component 64 to lock the dialysis catheter 58 to the guide catheter 32. In particular, the third locking component 72 includes a threaded cap which has a hole extending therethrough. The dialysis catheter 58 may extend through the hole as also shown in FIG. 10. The third locking component 72 further includes an upper tab and a lower tab each which extends around and is secured to the outer surface of the dialysis catheter 58. The threaded cap is interposed between the upper tab and the lower tab so as to be retained therebetween. The threaded cap is able to be rotated relative to the dialysis catheter in order to secure/release the dialysis catheter 58 to/from the guide catheter 32.

The dialysis catheter 58 further includes an egress line and an ingress line. The egress line is in fluid communication with the egress lumen, while the ingress line is in fluid communication with the ingress lumen. The egress line has an adapter attached thereto, and the ingress line has another adapter attached thereto. In addition, a clamp may be positioned on the egress line, while another clamp may positioned on the ingress line. It should be understood that closure of the above-identified clamps cause fluid communication between the above adapters and the above distal egress orifices to be prevented.

The dialysis catheter 58 may be positioned within the guide lumen 34 of the guide catheter 32 as shown in FIG. 10.

When the dialysis catheter 58 is positioned within the guide lumen 34 as shown in FIG. 10, the dialysis catheter is said to be positioned in an "inserted position." When the dialysis catheter 58 is entirely removed from the guide lumen 34, the dialysis catheter 58 is said to be positioned in a "removed position."

When the dialysis catheter 58 is positioned in the inserted position, a distal segment of the dialysis catheter 58 extends out of the distal guide orifice 36 of the guide catheter 32. Accordingly, the distal ingress orifice and the distal egress orifice of the dialysis catheter 58 are each positioned outside of guide lumen 34 when the dialysis catheter 58 is located in the inserted position. Moreover, when the dialysis catheter 58 is located in the inserted position, the threaded cap is positioned adjacent to the first locking component 64 such that the threaded cap can be rotated relative to guide catheter 32 so as to lock the third locking component 72 to the first locking component 64. Note that locking the third locking component 72 to the first locking component 64 in the above described manner locks the dialysis catheter 58 to the guide catheter 32.

During use of the catheter system 16, the guide catheter 32 is placed within the body 46 using the tunneled catheter technique. In particular a first opening is created by making a small incision in the skin 42 with a scalpel directly over the right internal jugular vein 24. Thereafter, the right internal jugular vein 24 is punctured to create a venotomy 88 at a location directly below the first opening by advancing a needle through the skin incision and the subcutaneous tissue 44 and into the right internal jugular vein 24. Thereafter, a guidewire is advanced through the needle into the right internal jugular vein 24 through the venotomy 88. The needle is then removed over the guidewire. One or more tubular vessel dilators is passed over the guidewire to widen the opening defined in the skin 42 and subcutaneous tissue 44, and further to widen the venotomy 88 defined in the wall of the right internal jugular vein 24 to a caliber similar to that of the tubular guide. Thereafter, the tubular guide is advanced over the guidewire and into the right internal jugular vein 24. Then, a second opening is created in the skin 42 which is spaced apart at least several centimeters from the first opening. A tunneling instrument is advanced from the second opening to the first opening so as to create a passageway within the subcutaneous tissue 44 under the skin 42 between the first opening and the second opening. The guide catheter 32 is then advanced into the second opening and through the passageway such that a distal end of the guide catheter 32 is located adjacent the first opening. The distal end of the guide catheter 32 is then inserted through the tubular guide member and into the right internal jugular vein 24 so that the tissue ingrowth member 38 is positioned in the subcutaneous tissue 44. Thereafter, the tubular guide member is removed. The first opening is then closed with suture whereby the guide catheter 32: (a) is no longer exposed through the first opening, (b) extends for at least several centimeters under the skin 42 between second opening and the venotomy 88, and (c) extend outs of the second opening so that the proximal end of the guide catheter 32 is located outside of the body 46.

Figure 7:
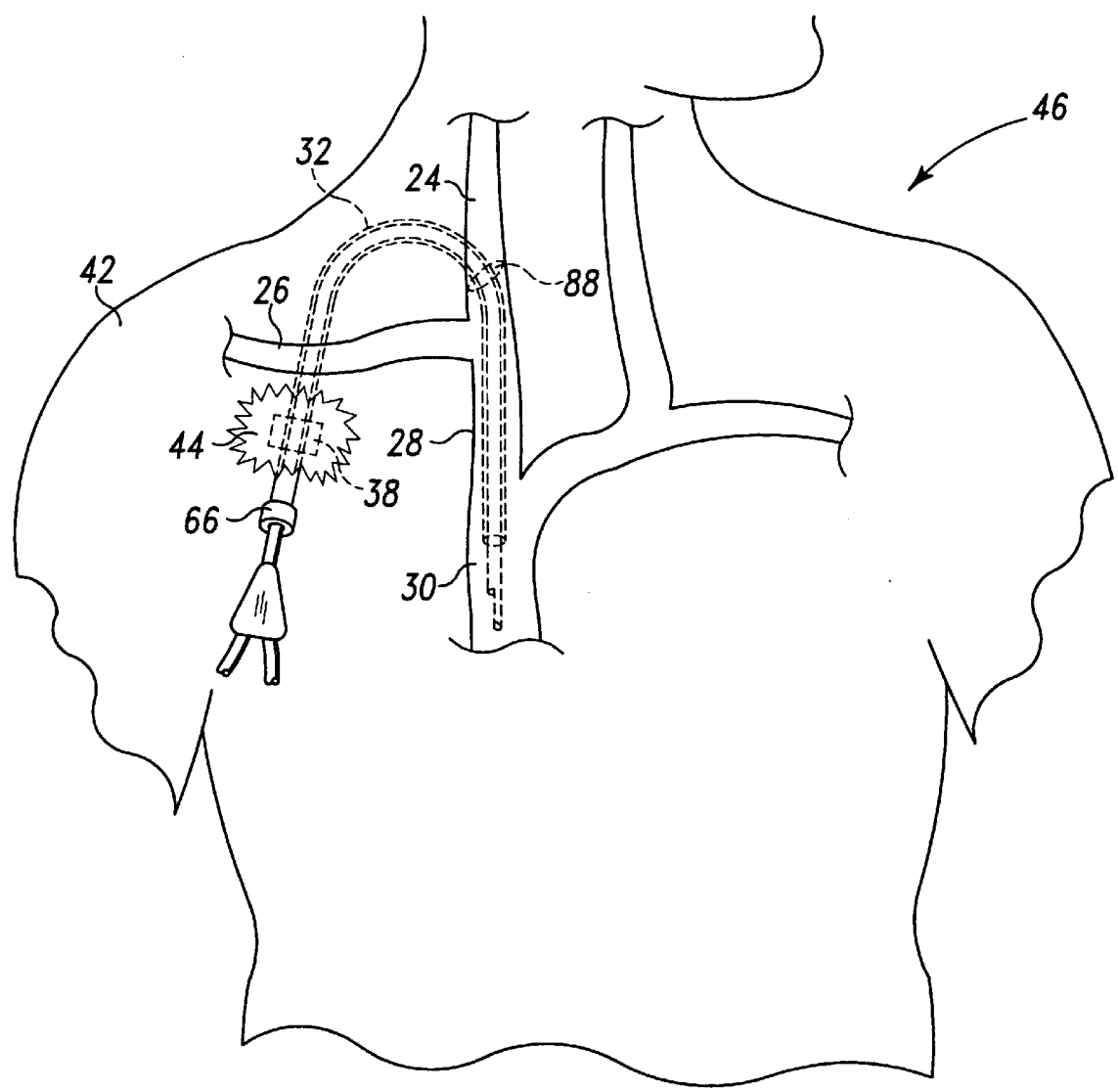
FIG. 7 is an enlarged view which is similar to FIG. 2, but showing the long-term dialysis catheter system (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right inominate vein and the superior vena cava.

Note that after the guide catheter 32 is placed in the vascular system 22 as described above, the guide catheter 32 is positioned in the right internal jugular vein 24, the right inominate vein 28, and the superior vena cava 30 as shown in FIG. 7. Moreover, note that as the tissue ingrowth member 38 remains in contact with the subcutaneous tissue 44 over a period of time, the subcutaneous tissue 44 becomes affixed to the tissue ingrowth member 38 thereby securing the guide catheter 32 to the body 46. As discussed above, affixation of the tissue ingrowth member 38 to the subcutaneous tissue 44 in the above described manner helps prevent bacterial migration up the guide catheter 32 from the first opening to the venotomy 88 thereby preventing serious infection.

Once the guide catheter 32 is placed in the body 46 as described above, the dialysis catheter 48 is advanced through the guide lumen 34 of the guide catheter 32 so that the distal ingress orifice 54 and the distal egress orifice 56 are advanced out of the distal guide orifice 36 and positioned within the superior vena cava 30 as shown in FIG. 7. (In other words, the dialysis catheter 48 is advanced to its inserted position.) The dialysis catheter 48 is then locked to guide catheter 32 utilizing the first locking component 64 and the second locking component in the above described manner.

When a patient desires to be dialyzed (i.e. engage in a dialysis session), egress line 78 and ingress line 80 are respectively connected to the inlet line 18 and the outlet line 20 of the hemodialysis machine 8 as shown in FIG. 1. A dialysis procedure is then performed on the patient's body 46 in a well known manner. Upon completion of the dialysis procedure, the egress line 78 and ingress line 80 are respectively disconnected from the inlet line 18 and the outlet line 20, and the patient is able to carry on about his/her business. Thereafter, when a patient desires to be dialyzed again, the above procedure is repeated. After a number of dialysis sessions, the lumens of the dialysis catheter 48 may become partially or even totally occluded due to blood clot build-up. In order to remedy this problem prior to continuing the dialysis sessions, the dialysis catheter 48 may be replaced with the dialysis catheter 58. In particular, the dialysis catheter 48 is unlocked from the guide catheter 32 and withdrawn from the guide lumen 34. Then, the dialysis catheter 58 is positioned within the guide lumen 34 of the guide catheter 32, and locked to the guide catheter 32. Thereafter, the dialysis sessions may be continued.

It should be understood that the blood flow valves 62 and 70 prevent blood from escaping through guide lumen 34 after the dialysis catheter 48 has been removed from guide catheter 32 and before dialysis catheter 58 is inserted into the guide catheter. Note also that the blood flow valves 62 and 70 also prevent air from entering the vascular system 22 through guide lumen 34 after the dialysis catheter 48 has been removed from guide catheter 32 and before dialysis catheter 58 is inserted into the guide catheter.

It should further be appreciated that during a dialysis session when either the dialysis catheter 48 or the dialysis catheter 58 is positioned within the guide lumen 32, the blood flow valves 62 and 70 function to prevent blood and/or air leakage through a space defined between the outer surface of the dialysis catheter 48, 58 and the inner surface of the guide catheter 32.

While the invention has been illustrated and described in detail in the drawings and foregoing description, the same is to be considered as illustrative and not restrictive in character, it being understood that only the preferred embodiment and method have been shown and described and that all changes and modifications that come within the spirit of the invention are desired to be protected.

For instance, the above-described tunneled catheter system utilized to perform hemodialysis (i.e. catheter system 16) can also be utilized to perform other medical procedures in which dual-lumen catheter access to the central venous system is required. An example of such other medical procedures is plasmapheresis in which blood is withdrawn from the vascular system, components of the blood are separated outside of the body, and a portion of the blood components are then returned to the vascular system.

Moreover, the above-described tunneled catheter system utilized to perform hemodialysis (i.e. catheter system 16) can be modified to perform medical procedures in which single-lumen catheter access to the vascular system is required. In particular, the dual lumen inner catheters 48, 58 of the catheter system 16 may be replaced with two single lumen catheters, and utilized in a manner similar to that described above with respect to the catheter system 16 (i.e. a first single lumen catheter is used until it is partially or fully occluded by clot, and thereafter it is replaced with a second unoccluded single lumen catheter). Examples of medical procedures in which single-lumen catheter access to the vascular system is required includes (i) chemotherapy or other long-term medicinal infusions, (ii) total parenteral nutrition, (iii) repetitive blood transfusions, and (iv) repetitive blood samplings.

In addition, another medical procedure which may be performed using the above tunneled catheter system (i.e. catheter system 16) or the above single-lumen modification of such catheter system is peritoneal dialysis. In particular, catheter occlusion may occur during peritoneal dialysis, and such occlusion may be eliminated in a manner similar to that described above with respect to the catheter system 16.

What is claimed is:

1. A method of maintaining blood flow in a long-term dialysis catheter system which includes (i) a guide catheter having a tissue ingrowth member secured thereto, (ii) an original dialysis catheter having an original distal ingress orifice and an original distal egress orifice, and (iii) a replacement dialysis catheter having a replacement distal ingress orifice and a replacement distal egress orifice, comprising the steps of:

advancing a guide catheter into a body of a patient so that (i) a distal guide orifice of the guide catheter is positioned within a blood vessel of the body, and (ii) the tissue ingrowth member is positioned in subcutaneous tissue of the body;

advancing the original dialysis catheter though a guide lumen of the guide catheter so that the original distal ingress orifice and the original distal egress orifice are advanced out of the distal guide orifice and positioned within the blood vessel;

performing an original dialysis procedure on the patient with the original dialysis catheter after the original dialysis catheter advancing step;

leaving the guide catheter within the body for a period of time sufficient to cause the subcutaneous tissue to become affixed to the tissue ingrowth member which is secured to the guide catheter;

removing the original dialysis catheter from the guide lumen of the guide catheter;

advancing the replacement dialysis catheter though the guide lumen of the guide catheter so that the replacement distal ingress orifice and the replacement distal egress orifice are advanced out of the distal guide orifice and positioned within the blood vessel; and performing a subsequent dialysis procedure on the patient with the replacement dialysis catheter after the replacement dialysis catheter advancing step.

2. The method of claim 1, wherein the guide catheter includes a blood flow valve configured to restrict blood and air flow through the guide lumen when neither the original dialysis catheter nor the replacement dialysis catheter is located within the guide lumen of the guide catheter, further comprising the step of:

restricting blood and air flow through the guide lumen with the blood flow valve after the original dialysis catheter removing step and before the replacement dialysis catheter advancing step.

3. The method of claim 1, further comprising the step of locking the original dialysis catheter to the guide catheter prior to the original dialysis procedure performing step and the guide catheter leaving step.

4. The method of claim 3, further comprising the step of unlocking the original dialysis catheter from the guide catheter prior to the original dialysis catheter removing step.

5. The method of claim 4, further comprising the step of locking the replacement dialysis catheter to the guide catheter prior to the subsequent dialysis procedure performing step.

6. A long-term dialysis catheter system for use in a body of a patient, comprising:

a guide catheter having a guide lumen defined therein, said guide lumen defining a distal guide orifice;

a tissue ingrowth member secured to an outer surface of said guide catheter and configured to facilitate fibrous tissue growth therein, whereby subcutaneous tissue of said body becomes affixed to said tissue ingrowth member when said tissue ingrowth member remains in contact with said subcutaneous tissue over a period of time;

an original dialysis catheter positionable between an original inserted position and an original removed position, wherein (i) said original dialysis catheter has an original ingress lumen and an original egress lumen defined therein, (ii) said original ingress lumen defines an original distal ingress orifice, and (iii) said original egress lumen defines an original distal egress orifice; and a replacement dialysis catheter positionable between a replacement inserted position and a replacement removed position, wherein (i) said replacement dialysis catheter has a replacement ingress lumen and a replacement egress lumen defined therein, (ii) said replacement ingress lumen defines a replacement distal ingress orifice, and (iii) said replacement egress lumen defines a replacement distal egress orifice, wherein said original distal ingress orifice and said original distal egress orifice are positioned on an original distal segment of said original dialysis catheter which extends out of said distal guide orifice of said guide catheter when said original dialysis catheter is positioned within said guide lumen of said guide catheter, and wherein said replacement ingress orifice and said replacement egress orifice are positioned on a replacement distal segment of said replacement dialysis catheter which extends out of said distal guide orifice of said guide catheter when said replacement dialysis catheter is positioned within said guide lumen of said guide catheter.

7. The long-term dialysis catheter system of claim 6, wherein said guide catheter includes a blood flow valve configured to restrict blood and air flow through said guide lumen of said guide catheter when neither said original dialysis catheter nor said replacement dialysis catheter is located within said guide lumen of said guide catheter.

8. The long-term dialysis catheter system of claim 6, wherein:

said guide catheter includes a first locking component, and said original dialysis catheter includes a second locking component which cooperates with said first locking component to lock said original dialysis catheter to said guide catheter.

9. The long-term dialysis catheter system of claim 8, wherein said replacement dialysis catheter includes a third locking component which cooperates with said first locking component to lock said replacement dialysis catheter to said guide catheter.

\* \* \* \* \*